(12) United States Patent
Reiley et al.

(10) Patent No.: US 7,166,121 B2
(45) Date of Patent: Jan. 23, 2007

(54) SYSTEMS AND METHODS USING EXPANDABLE BODIES TO PUSH APART CORTICAL BONE SURFACES

(75) Inventors: Mark A Reiley, Piedmont, CA (US); Arie Scholten, Fremont, CA (US); Karen D Talmadge, Palo Alto, CA (US)

(73) Assignee: Kyphon Inc., Sunnyvale, CA (US)

( * ) Notice: Subject to any disclaimer, the term of this patent is extended or adjusted under 35 U.S.C. 154(b) by 289 days.

(21) Appl. No.: 10/010,576

(22) Filed: Nov. 13, 2001

(65) Prior Publication Data

US 2002/0082608 A1 Jun. 27, 2002

Related U.S. Application Data

(63) Continuation of application No. 08/986,876, filed on Dec. 8, 1997, now abandoned, which is a continuation-in-part of application No. 08/871,114, filed on Jun. 9, 1997, now Pat. No. 6,248,110, which is a continuation-in-part of application No. 08/659,678, filed on Jun. 5, 1996, now Pat. No. 5,827,289, which is a continuation-in-part of application No. 08/485,394, filed on Jun. 7, 1995, now abandoned, which is a continuation-in-part of application No. 08/188,224, filed on Jan. 26, 1994, now abandoned.

(51) Int. Cl.
*A61M 29/00* (2006.01)
*A61F 2/28* (2006.01)
*A61B 19/00* (2006.01)

(52) U.S. Cl. .............. 606/192; 606/105; 128/898
(58) Field of Classification Search ........... 606/192, 606/57, 61, 86–88, 105, 58, 63, 68, 69, 70, 606/71; 600/207; 128/898
See application file for complete search history.

(56) References Cited

U.S. PATENT DOCUMENTS

| | | | | |
|---|---|---|---|---|
| 3,800,788 A | * | 4/1974 | White | 606/86 |
| 4,313,434 A | | 2/1982 | Segal | |
| 4,969,888 A | * | 11/1990 | Scholten et al. | 606/94 |
| 5,102,413 A | | 4/1992 | Poddar | |
| 5,108,395 A | * | 4/1992 | Laurain | 606/61 |
| 5,108,404 A | | 4/1992 | Scholten et al. | |
| 5,167,665 A | * | 12/1992 | McKinney | 606/69 |
| 5,331,975 A | | 7/1994 | Bonutti | |
| 5,423,850 A | | 6/1995 | Berger | |
| 5,788,703 A | | 8/1998 | Mittelmeier et al. | |
| 5,897,557 A | * | 4/1999 | Chin et al. | 606/71 |

* cited by examiner

Primary Examiner—Julian W. Woo
(74) Attorney, Agent, or Firm—Ryan Kromholz & Manion, S.C.

(57) ABSTRACT

Systems and methods insert an expandable body in a collapsed configuration into a space defined between cortical bone surfaces. The space can, e.g., comprise a fracture or an intervertebral space. The systems and methods cause expansion of the expandable body within the space, thereby pushing apart the cortical bone surfaces to, e.g., reduce the fracture or push apart adjacent vertebral bodies as part of a therapeutic procedure.

5 Claims, 6 Drawing Sheets

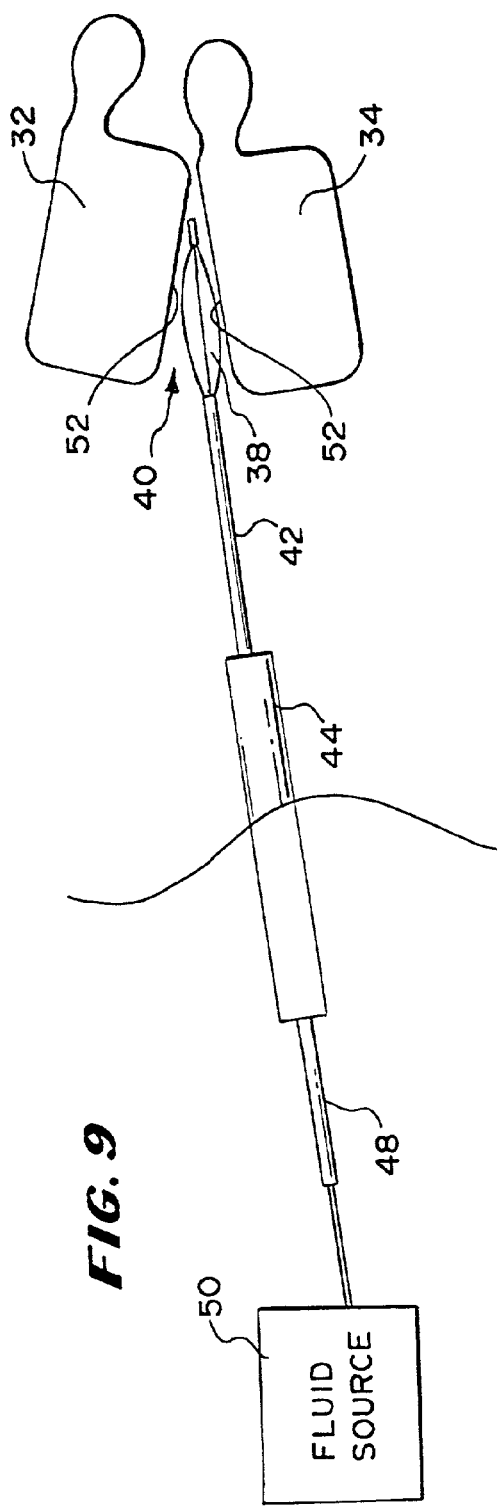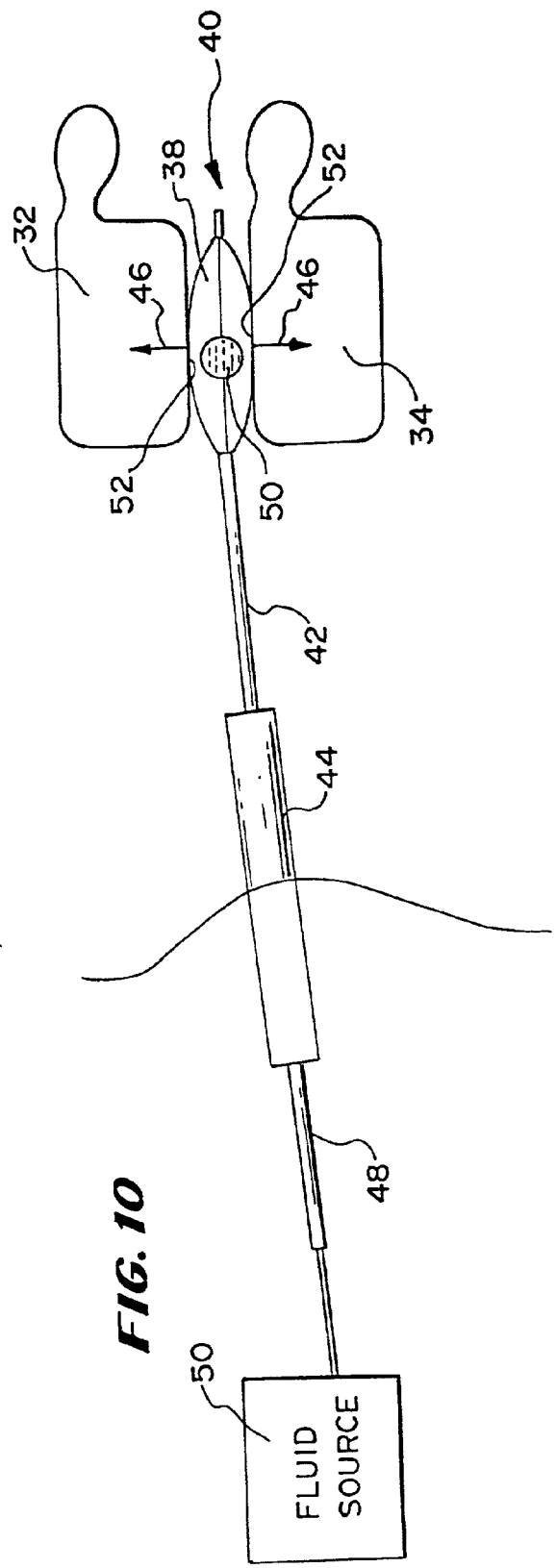

SYSTEMS AND METHODS USING EXPANDABLE BODIES TO PUSH APART CORTICAL BONE SURFACES

RELATED APPLICATIONS

This application is a continuation of U.S. patent application Ser. No. 08/986,876, filed 8 Dec. 1997, now abandoned, and entitled "Systems and Methods Using Expandable Bodies to Push Apart Cortical Bone Surfaces," which is a continuation-in-part of U.S. patent application Ser. No. 08/871,114, filed Jun. 9, 1997, now U.S. Pat. No. 6,248,110, and entitled "Systems and Methods for Treatment of Fractured or Diseased Bone Using Expandable Bodies," which is a continuation-in-part of U.S. patent application Ser. No. 08/659,678, filed Jun. 5, 1996, now U.S. Pat. No. 5,827,289, which is a continuation-in-part of U.S. patent application Ser. No. 08/485,394, filed Jun. 7, 1995, now abandoned, which is a continuation-in-part of U.S. patent application Ser. No. 08/188,224, filed Jan. 26, 1994, now abandoned, entitled, "Improved Inflatable Device For Use In Surgical Protocol Relating To Fixation Of Bone."

FIELD OF THE INVENTION

The invention relates to the treatment of bone conditions in humans and other animals.

BACKGROUND OF THE INVENTION

There are 2 million fractures each year in the United States. There are also other bone diseases involving infected bone, poorly healing bone, or bone fractured by severe trauma. These conditions, if not successfully treated, can result in deformities, chronic complications, and an overall adverse impact upon the quality of life.

SUMMARY OF THE INVENTION

The invention provides improved systems and methods for treating bone using one or more expandable bodies. The systems and methods insert an expandable body in a collapsed configuration into a space defined between cortical bone surfaces. The space can, e.g., comprise a fracture or an intervertebral space left after removal of the disk between two vertebral bodies. The systems and methods cause expansion of the expandable body within the space, thereby pushing apart the cortical bone surfaces. The expansion of the body serves, e.g., to reduce the fracture or to push apart adjacent vertebral bodies as part of a therapeutic procedure, so that healing can occur without deformity.

Features and advantages of the inventions are set forth in the following Description and Drawings, as well as in the appended claims.

BRIEF DESCRIPTION OF THE DRAWINGS

FIG. 9 shows a view of the vertebral bodies shown in FIG. 8, with an expandable body deployed in a collapsed geometry between the facing cortical bone surfaces between the vertebral bodies;

FIG. 10 shows a view of the vertebral bodies shown in FIG. 9, with the expandable body expanded to exert pressure against the facing cortical bone surfaces, pushing the vertebral bodies apart to restore a normal anatomic condition, which can be healed without deformity.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The use of expandable bodies to treat bones is disclosed in U.S. Pat. Nos. 4,969,888 and 5,108,404. The systems and methods disclosed in these patents treat bone from the inside out. That is, the systems and methods deploy an expandable body into the interior volume of the bone. Expansion of the body inside the bone compacts or compresses surrounding cancellous bone. The compaction of cancellous bone inside the bone exerts interior force upon outside cortical bone, making it possible to elevate or push broken and compressed cortical bone back to or near its original prefracture position.

Figure 1:
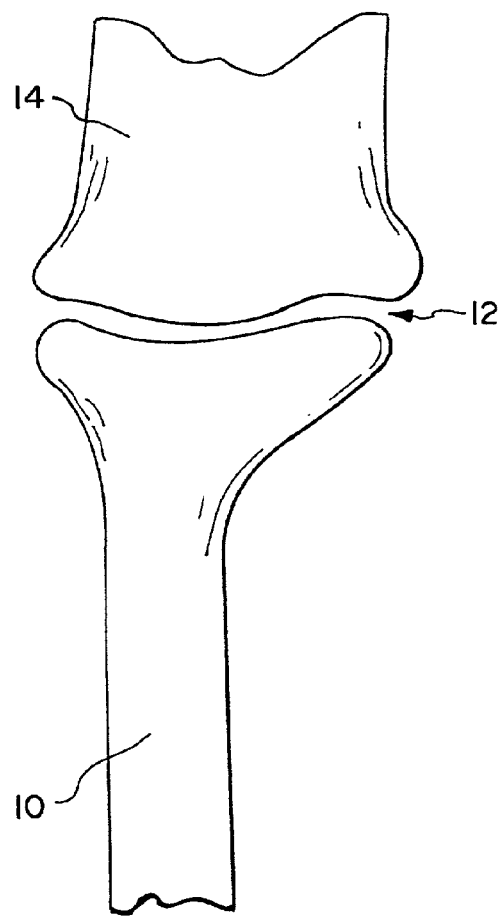
FIG. 1 is a lateral view of a portion of a distal radius and humerus adjoining at the elbow in their normal anatomic condition.
Figure 2:
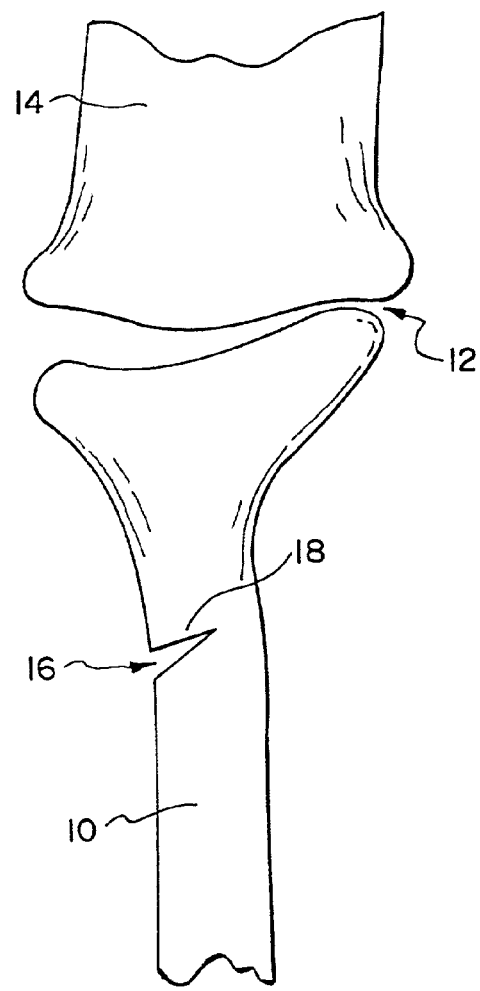
FIG. 2 is a lateral view of the distal radius and humerus shown in FIG. 1, except that the distal radius includes a fracture along which facing cortical bone surfaces have collapsed, creating a deformed condition.

There are times, however, when fracture reduction is indicated by applying external pressure directly on cortical bone surfaces. FIGS. 1 and 2 exemplify one representative circumstance.

FIG. 1 shows a normal human distal radius 10, near the elbow joint 12, where the radius 10 adjoins the humerus 14. FIG. 2 shows a fracture 16 in the distal radius 10. The fracture 16 can be caused by bone disease or trauma. As FIG. 2 shows, cortical bone surfaces 18 surrounding the fracture 16 have collapsed upon themselves, moving the radius 10 out of normal alignment with the humerus 14. It is not desirable to allow the cortical bone surfaces 18 to heal or fuse in a collapsed condition, as deformity and discomfort can result.

Figure 3:
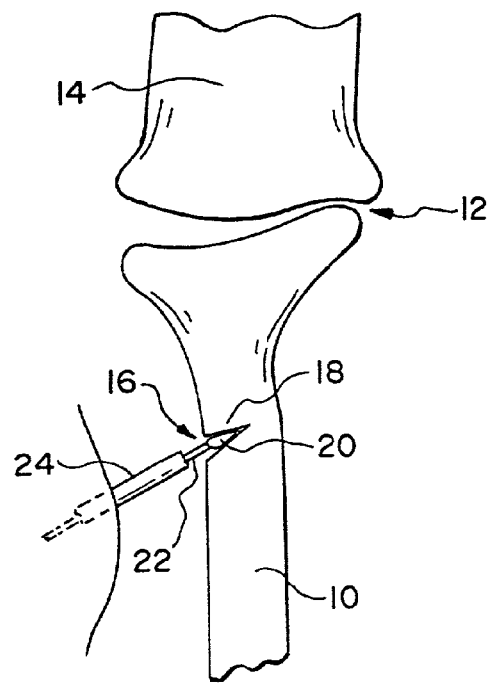
FIG. 3 shows a lateral view of the distal radius and humerus shown in FIG. 2, with an expandable body deployed in a collapsed geometry between the collapsed cortical bone surfaces.
Figure 4:
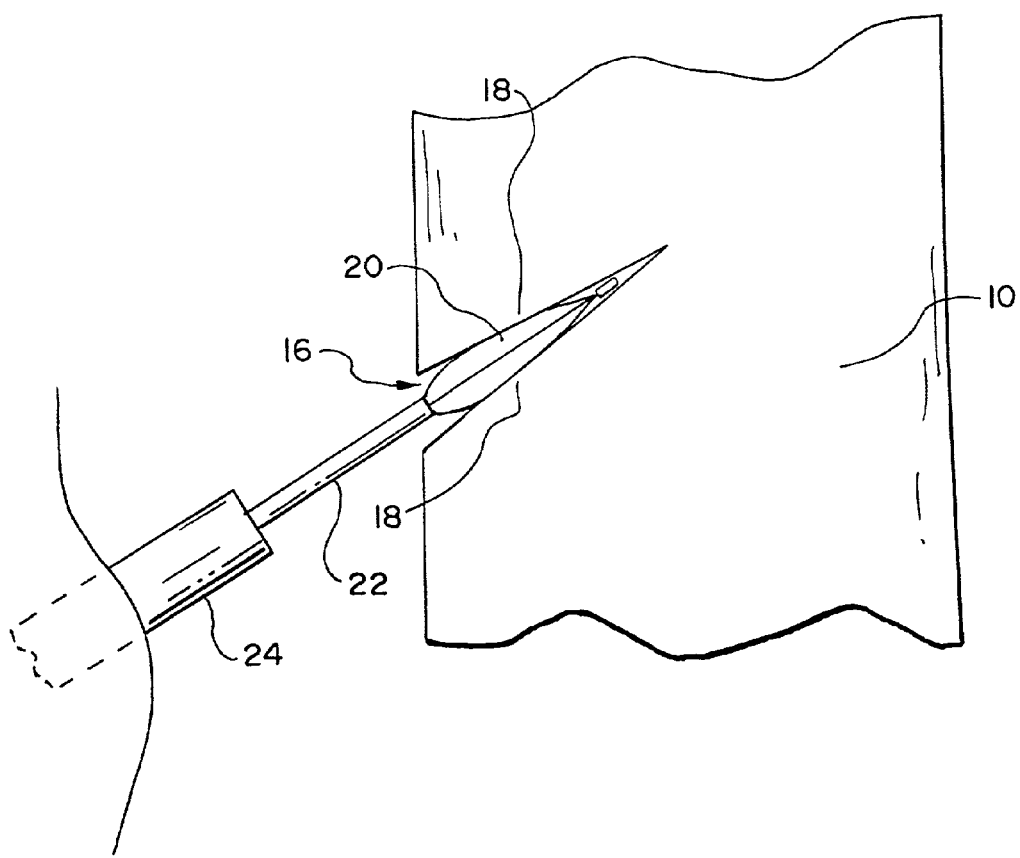
FIG. 4 is an enlarged view of the deployment of the expandable body deployed between the collapsed cortical bone surfaces as shown in FIG. 3.

According to the invention (as FIGS. 3 and 4 show), an expandable body 20 is positioned in the fracture between the facing cortical bone surfaces 18. FIGS. 3 and 4 show the expandable body 20 in a collapsed condition, which aids its deployment and placement in the fracture 16.

Access can be achieved either with a closed, minimimally invasive procedure or with an open procedure. FIG. 3 shows the expandable body 20 carried at the distal end of a catheter tube 22. The catheter tube 22 is introduced through conventional percutaneous deployment through a guide tube or cannula 24, under radiologic or CT monitoring.

The materials for the catheter tube 22 are selected to facilitate advancement of the body 20 into position against the cortical bone surfaces 18 through the cannula 24. The catheter tube 22 can be constructed, for example, using standard flexible, medical grade plastic materials, like vinyl, nylon, polyethylenes, ionomer, polyurethane, and polyethylene tetraphthalate (PET). The catheter tube 22 can also include more rigid materials to impart greater stiffness and thereby aid in its manipulation. More rigid materials that can be used for this purpose include Kevlar™ material, PEBAX™ material, stainless steel, nickel-titanium alloys (Nitinol™ material), and other metal alloys.

Figure 5:
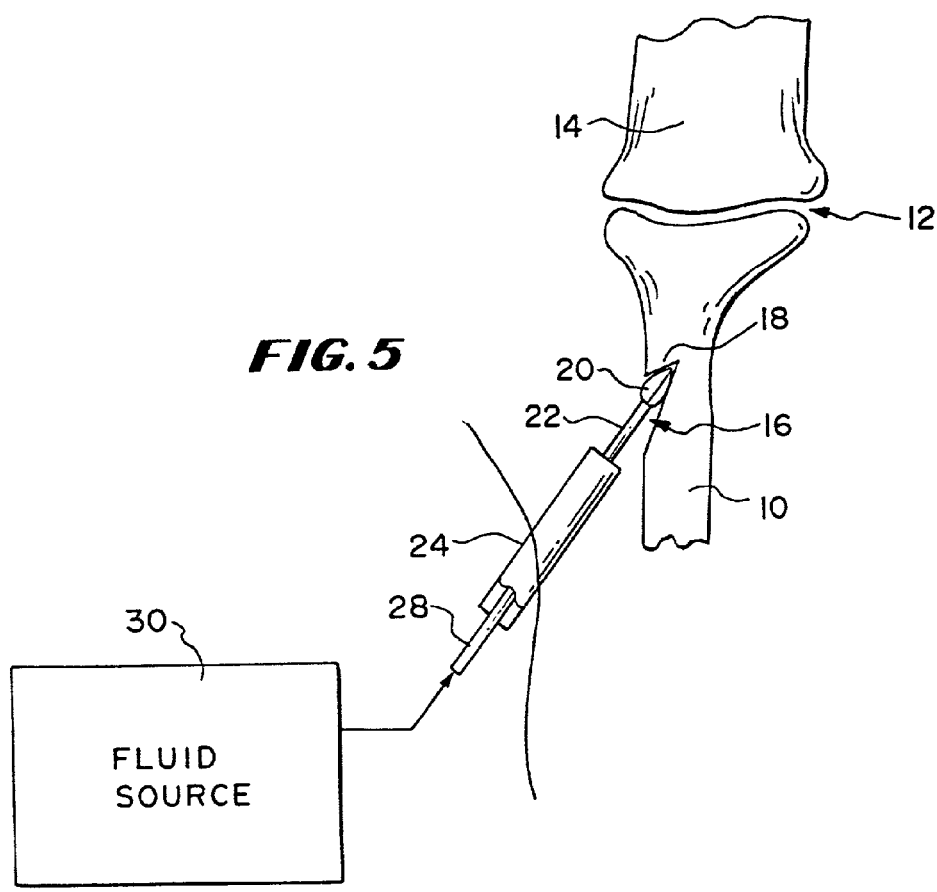
FIG. 5 shows a view of the distal radius and humerus shown in FIG. 3, with the expandable body expanded to exert pressure against the collapsed cortical bone surfaces, pushing them apart to restore a normal anatomic condition, so that the distal radius can heal without deformity.
Figure 6:
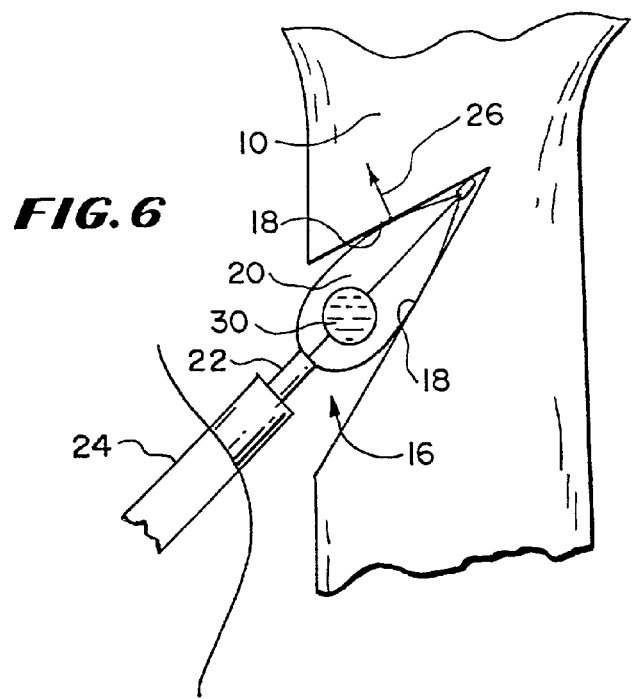
FIG. 6 is an enlarged view of the expanded body pushing the cortical bone surfaces apart, as shown in FIG. 5.

The body 20 is caused to assume an expanded geometry within the fracture 16, which is shown in FIGS. 5 and 6. To provide expansion of the body 20, the catheter tube 22 includes an interior lumen 28. The lumen 22 is coupled at the proximal end of the catheter tube 22 to a source of fluid 30. The fluid 30 is preferably radio-opaque to facilitate visualization. For example, Renograff™ can be used for this purpose.

The lumen 28 conveys the fluid 30 into the body 20. As fluid 30 enters the body 20, the body 20 expands, as FIGS. 5 and 6 show. Because the fluid 30 is radio-opaque, body expansion can be monitored fluoroscopically or under CT visualization. Using real time MRI, the body 20 may be filled with sterile water, saline solution, or sugar solution.

Expansion of the body 20 exerts pressure directly against surrounding the cortical bone surfaces 18. The pressure exerted by expanding body 20 moves surrounding the cortical bone surfaces 18 apart at the fracture 16. The exerted pressure lifts surrounding cortical bone surfaces 18 at the fracture 16 (shown by arrow 26 in FIG. 6) out of the deformed, collapsed condition, back to or near the original prefracture position. The expandable body 20 thereby realigns the cortical bone surfaces 18 at the fracture 16 by the application of direct external pressure, e.g., to allow the bone to heal at or near its anatomic normal orientation by the application of conventional exterior casting or other conventional interior or exterior fixation devices.

Figure 7:
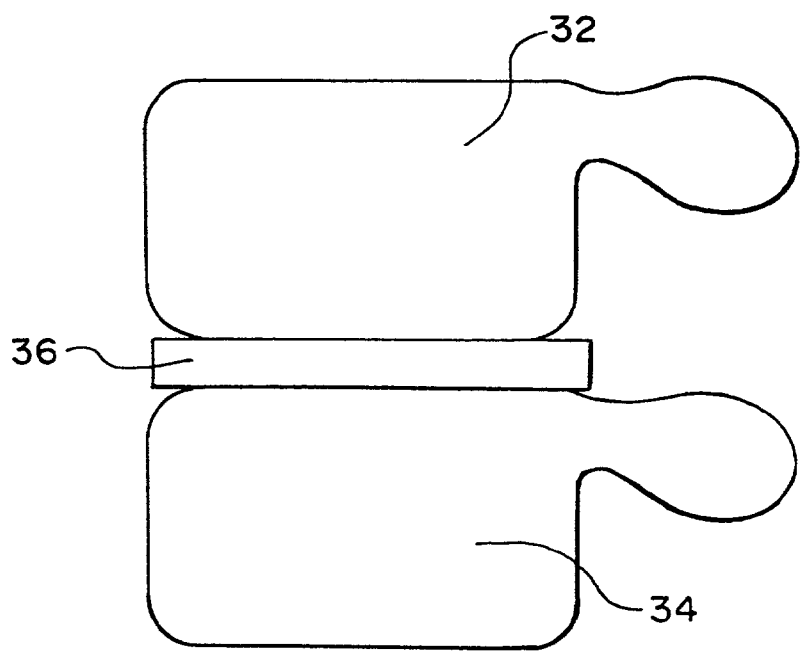
FIG. 7 is a lateral view of two vertebral bodies and intervertebral disk in their normal anatomic condition.
Figure 8:
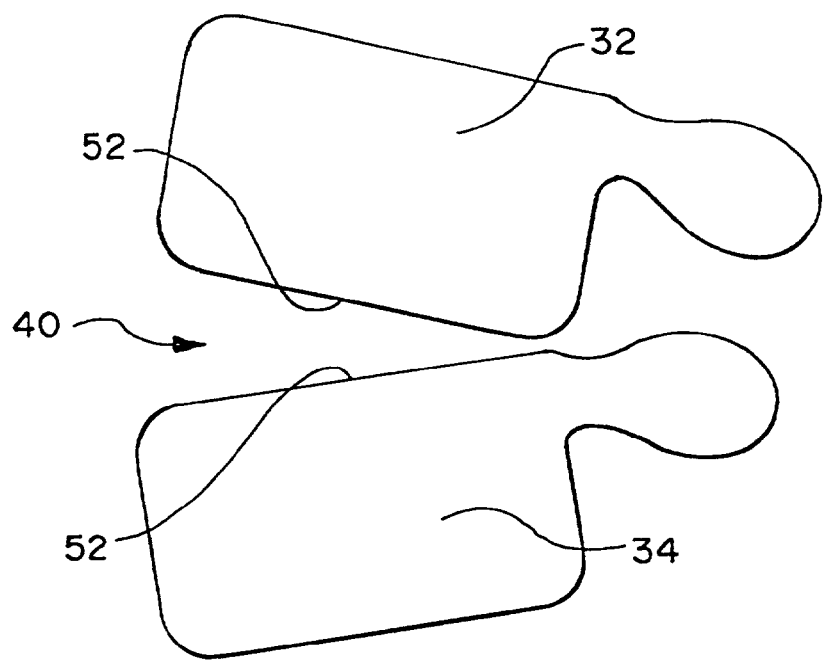
FIG. 8 is a view of the two vertebral bodies shown in FIG. 7, except that the intervertebral disk has been removed and the vertebral bodies have shifted out of normal orientation, creating a deformed condition.

FIGS. 7 and 8 exemplify another circumstance where force applied by an expandable body directly against facing cortical bone surfaces may be indicated for therapeutic purposes. FIG. 7 shows two adjacent vertebral bodies 32 and 34, separated by a healthy intervertebral disk 36 in a normally aligned condition. FIG. 8 shows the adjacent vertebral bodies 32 and 34 after disease or injury has necessitated the removal of the intervertebral disk 36. The absence of the disk 36 in FIG. 8 has caused the vertebral bodies to shift out of normal alignment into a deformed orientation.

As FIG. 9 shows, an expandable body 38 has been positioned between the vertebral bodies 32 and 34, in the space 40 the disk 36 once occupied. FIG. 9 shows the deployment of the expandable body 38 at the distal end of a catheter tube 42, through a cannula 44, under radiologic or CT monitoring. As before stated, access can be achieved either with a closed, minimimally invasive procedure (as FIG. 9 contemplates) or with an open procedure.

The catheter tube 42 includes an interior lumen 48, which is coupled at the proximal end of the catheter tube 42 to a source of fluid 50 (which is preferably radio-opaque, such as Renograffin™). The lumen 48 conveys the fluid 50 into the body 38 to cause it to expand. As FIG. 10 shows, expansion of the body 38 exerts pressure directly against the facing cortical bone surfaces 52 of the two vertebral bodies 32 and 34. The pressure exerted by the body 38 moves the cortical bone surfaces 52 apart about the intervertebral space 40, as shown by arrows 46 in FIG. 10. The pressure exerted against the cortical bone surfaces 52 lifts the vertebral bodies 32 and 34 out of the deformed condition, back to or near their original position. The direct pressure exerted by the body 38 on the cortical bone surfaces 52 pushes the vertebral bodies 32 and 34 apart to allow placement of a disk prosthesis, or medication, or to allow fusion to occur without deformity by the application of conventional interior or exterior fixation devices.

Figure 11:
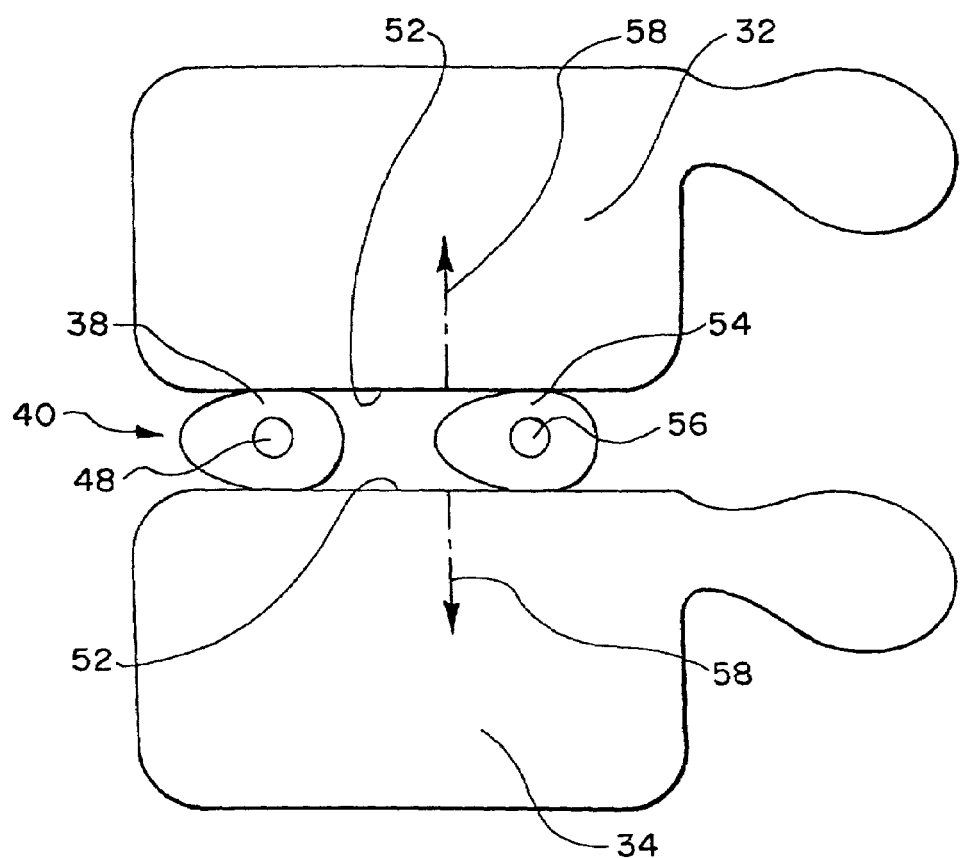
FIG. 11 shows a view of the vertebral bodies shown in FIG. 9, with two expandable bodies deployed in the intervertebral space to exert pressure to push the vertebral bodies apart to promote healing without deformity.

It should be appreciated that, in the embodiments shown, the use of more than one expandable body 20 or 38 may be indicated to move the targeted surfaces of cortical bone apart. For example, as FIG. 11 shows, a second expandable body 54 has been positioned in the space 40 with the first mentioned expandable body 38. The second expandable body 54 can be carried by the same catheter tube 42 as the first expandable body 38, or it can be carried by a separate catheter tube (not shown). A lumen 56 conveys the fluid 50 into the second expandable body 54, causing it to expand, in the same way that the first expandable body 38 expands in the space 40. As FIG. 11 shows, joint expansion of the bodies 38 and 54 in the space 40 exerts pressure against the facing cortical bone surfaces 52 of the two vertebral bodies 32 and 34. The pressure exerted by the two bodies 38 and 54 moves the cortical bone surfaces 52 apart about the intervertebral space 40, as shown by arrows 58 in FIG. 11. The pressure exerted by the two expandable bodies 38 and 54 lifts the vertebral bodies 32 and 34 out of the deformed condition, back to or near their original position, to allow placement of a disk prosthesis, or medication, or to allow fusion to occur without deformity by the application of conventional interior or exterior fixation devices.

The material of the expandable body or bodies used can be selected according to the therapeutic objectives surrounding its use. For example, materials including vinyl, nylon, polyethylenes, ionomer, polyurethane, and polyethylene tetraphthalate (PET) can be used. The thickness of the body wall 58 is typically in the range of $2/1000$ths to $25/1000$ths of an inch, or other thicknesses that can withstand pressures of up to, for example, 250–500 psi.

If desired, the material for the expandable body or bodies can be selected to exhibit generally elastic properties, like latex. Alternatively, the material can be selected to exhibit less elastic properties, like silicone. Using expandable bodies with generally elastic or generally semi-elastic properties, the physician monitors the expansion to assure that over-expansion and body failure do not occur. Furthermore, expandable bodies with generally elastic or generally semi-elastic properties may require some form of external or internal restraints. For example, the material for the body can be selected to exhibit more inelastic properties, to limit expansion of the wall 58 prior to wall failure. The body can also include one or more restraining materials, particularly when the body is itself made from more elastic materials.

The restraints, made from flexible, inelastic high tensile strength materials, limit expansion of the body prior to failure.

When relatively inelastic materials are used for the body, or when the body is otherwise externally restrained to limit its expansion prior to failure, a predetermined shape and size can be imparted to the body, when it is substantially expanded. The shape and size can be predetermined according to the shape and size of the surrounding cortical bone. The shape of the surrounding cortical bone and the presence of surrounding local anatomic structures are generally understood by medical professionals using textbooks of human skeletal anatomy, along with their knowledge of the site and its disease or injury. The physician is also able to select the materials and geometry desired for the body based upon prior analysis of the morphology of the targeted bone using, for example, plain films, spinous process percussion, or MRI or CRT scanning. The objective is to push cortical bone surfaces apart to meet the therapeutic objectives without harm. By definition, harm results when expansion of the body results in a worsening of the overall condition of the bone and surrounding anatomic structures, for example, by injury to surrounding tissue or causing a permanent adverse change in bone biomechanics.

It should be appreciated that expandable bodies as described possess the important attribute of being able to push apart cortical bone in fractured or deformed bone structures, back to or near normal anatomic position. This attribute makes these expandable bodies well suited for the successful treatment of fractures or deformities in the spine, as well as throughout the appendicular skeleton, such as the distal radius, the proximal humerus, the tibial plateau, the femoral head, hip, and calcaneus.

The features of the invention are set forth in the following claims.

We claim:

1. A method comprising
selecting for treatment a bone that includes a fractured exterior cortical bone region defined between facing exterior cortical bone surfaces that have collapsed upon themselves to displace away from a desired anatomic orientation an unfractured exterior cortical bone region remote from the fractured exterior cortical bone region,
deploying an expandable body having a collapsed condition sized and configured for insertion between the facing exterior cortical bone surfaces of the fractured exterior cortical bone region, and
enlarging the expandable body into an enlarged condition between the facing exterior cortical bone surfaces of the fractured exterior cortical bone region to lift the collapsed exterior facing cortical bone surfaces in the fractured exterior cortical bone region apart to move the unfractured exterior cortical bone region toward the desired anatomic orientation.

2. A method according to claim 1
wherein the expandable body is deployed on a distal end of an elongated body.

3. A method according to claim 1
wherein the expandable body is deployed in a collapsed condition through a percutaneous access path for insertion between the facing exterior cortical bone surfaces of the fractured exterior cortical bone region.

4. A method according to claim 1
wherein the expandable body is enlarged by fluid pressure.

5. A method according to claim 1
wherein the expandable body is enlarged by inflation.

* * * * *